(12) United States Patent
Jiang et al.

(10) Patent No.: US 6,953,671 B2
(45) Date of Patent: Oct. 11, 2005

(54) PLASMA PHOSPHOLIPID TRANSFER PROTEIN (PLTP) DEFICIENCY REPRESENTS AN ANTI-ATHEROGENIC STATE AND PLTP INHIBITOR HAS ANTI-ATHEROSCLEROSIS ACTION

(75) Inventors: Xian-Cheng Jiang, Fort Lee, NJ (US); Alan R. Tall, Cresskill, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/792,448

(22) Filed: Feb. 23, 2001

(65) Prior Publication Data

US 2002/0142280 A1 Oct. 3, 2002

(51) Int. Cl.[7] .............................. C12Q 1/48; C12Q 1/00; C12Q 1/29; C12Q 1/37; A01N 43/42
(52) U.S. Cl. ................................ 435/15; 435/4; 435/29; 435/23; 435/24; 514/310
(58) Field of Search ................................ 435/15, 4, 29, 435/23, 24; 514/310

(56) References Cited

U.S. PATENT DOCUMENTS 5,610,019 A * 3/1997 Day et al. ..................... 435/7.1
5,919,795 A * 7/1999 Chang et al. ................ 514/310

OTHER PUBLICATIONS

Notification of Transmittal of International Preliminary Examination Report issued by International Preliminary Examining Authority on Dec. 10, 2003 in connection with related International Application No. PCT/US02/05694.

Ginsberg, H.N. Role of lipid synthesis, chaperone proteins and proteasomes in the assembly and secretion of apoprotein B–containing lipoproteins from cultured liver cells. *Clin. Exp. Pharmacol. Physiol.* 24, A29–32 (1997).

Goldstein, J.L., & Brown, M.S. Familial hypercholesterolemia. In The Metabolic Basis of Inherited Disease. C.R. Scriver, A.R. Beaudet, W.S. Sly, D. Valle, J.B. Stanbury, J.B. Wyngaarden and D.S. Frederickson, editors, McGraw–Hill, New York, 1215–1250 (1989).

Hamilton, R.L. et al. Chylomicron–sized lipid particles are formed in the setting of apolipoprotein B deficiency. *J. Lipid Res.* 39, 1543–1557 (1998).

Havel, R.J. & Kane, J.P. Introduction: structure and metabolism of plasma lipoproteins. In The Metabolic Basis of Inherited Disease. Scriver, C. R. Beaudet, A.R. Sly, W.S. Valle, D. Standbury, J.B. Wyngaarden, J.B. & Frederickson, D.S. editors McGraw–Hill, New York, 1129–1138 (1989).

Jiang, X. –C. et al. Targeted mutation of plasma phospholipid transfer protein gene markedly reduces high–density lipoprotein levels. *J. Clin. Invest.* 103, 907–914 (1999).

Kane, J.P. & Havel R.J. Disorders of the biogenesis and secretion of lipoproteins containing the B apolipoproteins. In The Metabolic Basis of Inherited Disease. C.R. Scriver, A.R. Beaudet, W.S. Sly, D. Valle, J.B. Standbury, J.B. Wyngaarden and D.S. Frederickson, editors, McGraw–Hill, New York, 1139–1164 (1989).

Mahley, R.W. Apolipoprotein E: cholesterol transport protein with expanding role in cell biology. *Science* 240, 622–630 (1988).

(Continued)

*Primary Examiner*—Louise N. Leary
(74) *Attorney, Agent, or Firm*—John P. White, Esq.; Cooper & Dunham LLP

(57) ABSTRACT

This invention provides methods of decreasing apolipoprotein B-containing lipoprotein and of treating atherosclerotic diseases and dyslipidemic diseases by reducing plasma phospholipid transfer protein activity, and methods of identifying chemical compounds for use in such treatments.

20 Claims, 5 Drawing Sheets

OTHER PUBLICATIONS

Okamoto, H. et al. A cholesteryl ester transfer protein inhibitor attenuates atherosclerosis in rabbits. *Nature* 496, 203–207 (Jul., 2000).

Plump, A.S. et al. Severe hypercholesterolemia and atherosclerosis in apolipoprotein E–deficient mice created by homologous recombination in ES cells. *Cell* 71, 343–353 (1992).

Plump, A.S. & Breslow, J.L. Apolipoprotein E and the apolipoprotein E–deficient mouse. *Annu. Rev. Nutr.* 15, 495–518 (1995).

Tall, A.R. Plasma lipid transfer proteins. *Annu. Rev. Biochem.* 64, 235–257 (1995).

Tall, A.R., Abreu, E. & Shuman, J. Separation of a plasma phospholipid transfer protein from cholesteryl ester/phospholipid exchange protein. *J. Biol. Chem.* 258, 2174–2180 (1983).

Twisk, J. et al. The role of the LDL receptor in apolipoprotein B secretion. *J. Clin. Invest.* 105(4), 521–532 (2000).

Wetterau, J.R. et al. Absence of microsomal triglyceride transfer protein in individuals with abetalipoproteinemia. *Science* 258, 999–1001 (1992).

Young, S.G. Recent progress in understanding apolipoprotein B. *Circulation* 82, 1574–1594 (1990).

Zhang, S.H. et al. Spontaneous hypercholesterolemia and arterial lesions in mice lacking apolipoprotein E. *Science* 258, 468–471 (1992).

\* cited by examiner

Fig 2
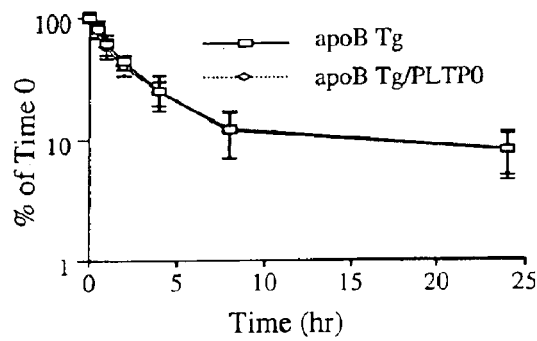
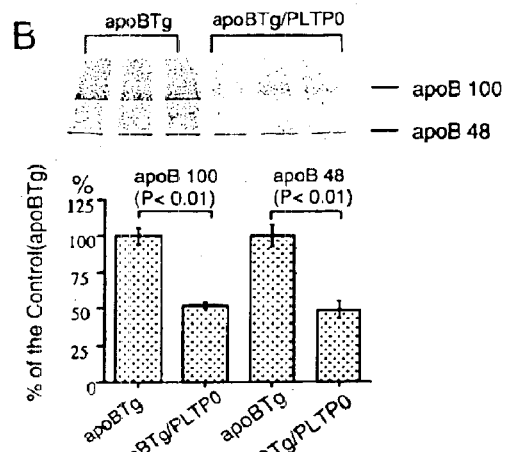
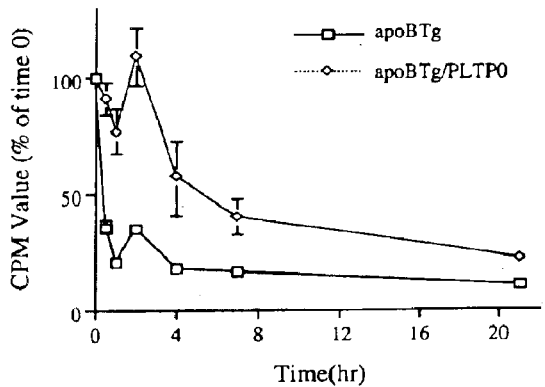
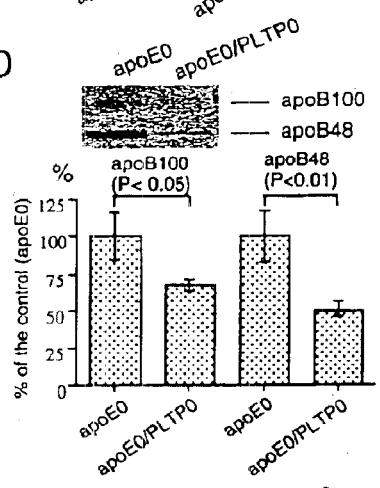
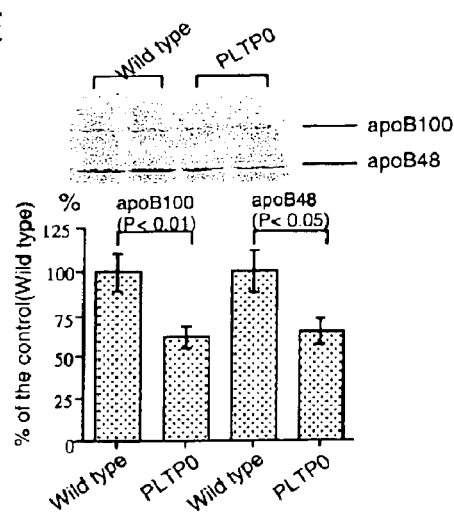
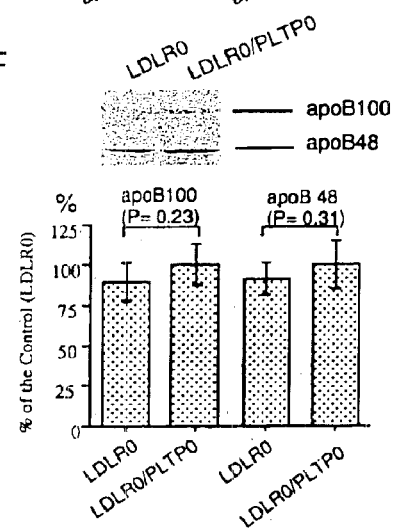

Fig. 4
A 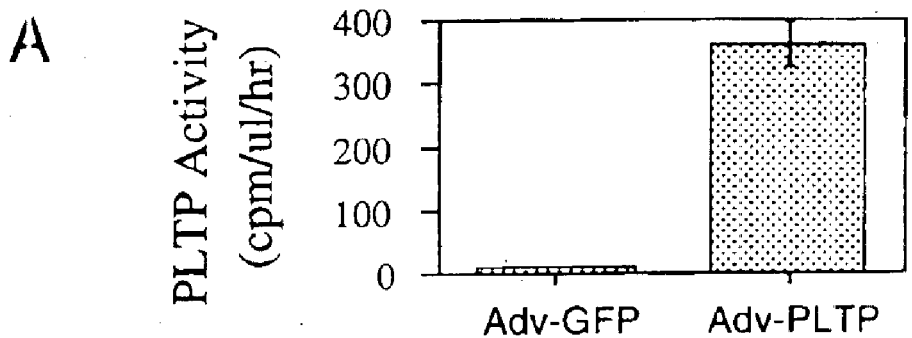
B 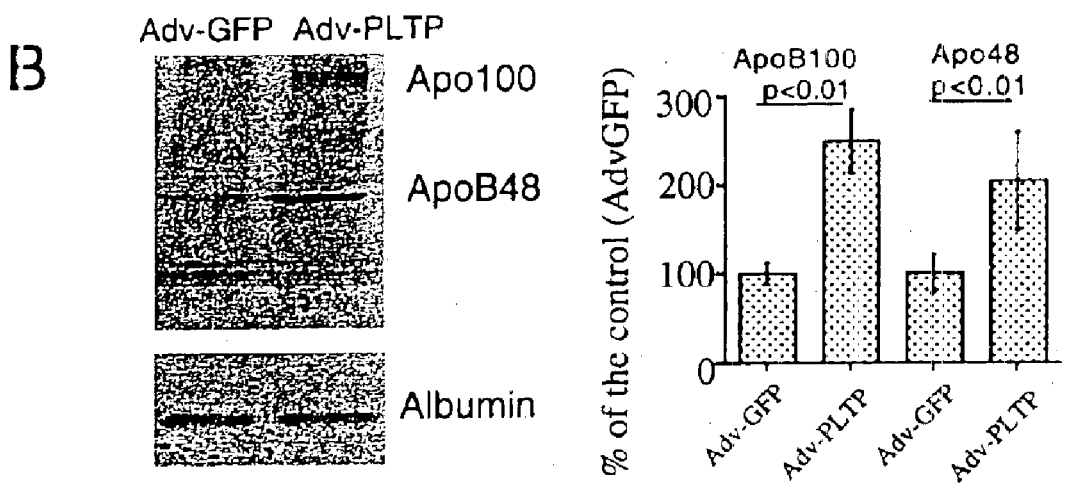
C 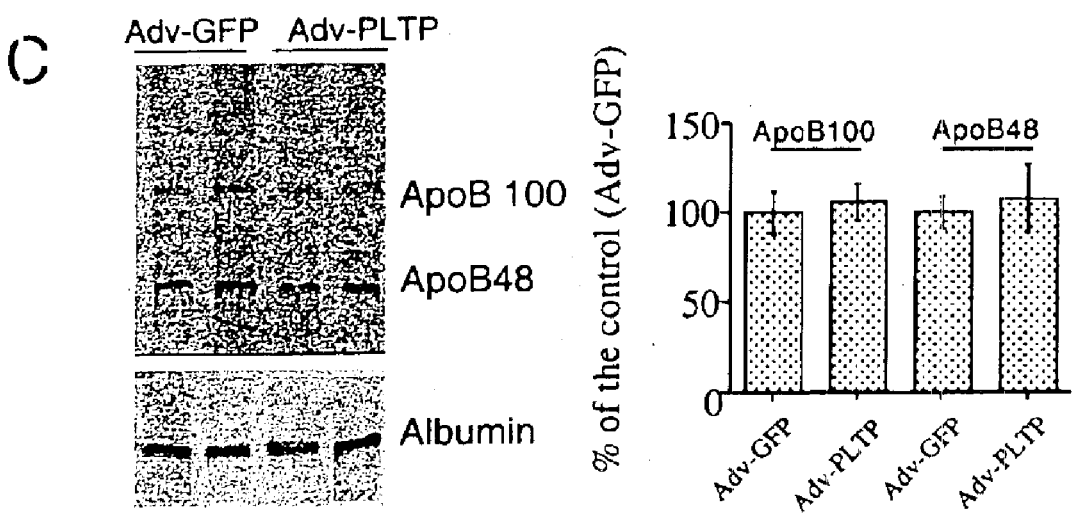

PLASMA PHOSPHOLIPID TRANSFER PROTEIN (PLTP) DEFICIENCY REPRESENTS AN ANTI-ATHEROGENIC STATE AND PLTP INHIBITOR HAS ANTI-ATHEROSCLEROSIS ACTION

The invention disclosed herein was made with Government support under grant HL54591 from the National Institutes of Health, U.S. Department of Health and Human Services. Accordingly, the U.S. Government has certain rights in this invention.

BACKGROUND OF THE INVENTION

Throughout this application, various publications are referenced by number. Full citations for these references may be found at the end of the specification immediately preceding the claims. The disclosures of these publications in their entireties are hereby incorporated by reference into this application to more fully describe the state of the art to which this invention pertains.

The regulation of the secretion of apolipoprotein B-containing lipoproteins is a topic of great importance, since their increased secretion plays a major role in dyslipidemia such as occurs in familial combined hyperlipidemia, diabetes and obesity.

Apolipoprotein B (apoB) is the major protein component of chylomicrons and very low density lipoprotein (VLDL) which transport triglycerides from the intestine and liver, respectively, into the bloodstream[1,2]. Intravascular remodeling of VLDL by lipolysis and lipid transfer results in the formation of low density lipoprotein (LDL), the major atherogenic lipoprotein in human plasma[3]. The overproduction of apolipoprotein B-containing lipoproteins (BLp) by the liver is thought to be a major cause of accelerated atherosclerosis. Increased hepatic BLp synthesis is the principal defect in subjects with familial combined hyperlipidemia[7,8], and is also an important component of the dyslipidemia of diabetes and obesity[9,10].

The regulation of BLp secretion, which takes place primarily on a post-transcriptional level[11], is poorly understood. Apolipoprotein B exists in two forms, apoB100 and apoB48[4]. Both are products of a single gene encoding a 14 Kb mRNA and share the same amino-terminal 2152 amino acids. Specific editing of human apoB100 mRNA in the intestine introduces a stop codon at residue 2153 to produce apoB48[5,6]. The addition of lipid to apolipoprotein B in the secretory pathway of hepatocytes and enterocytes is a tightly coordinated event. The microsomal triglyceride transfer protein (MTP) is involved in an early phase of lipid addition to apolipoprotein B, and deficiency of MTP results in markedly reduced secretion and levels of BLp in human abetalipoproteinemia[12,13].

During the intravascular lipolysis of chylomicrons and VLDL, there is transfer of excess surface phospholipids from these particles into high density lipoproteins (HDL)[14]. This process is mediated by a plasma phospholipid transfer protein (PLTP). Studies in PLTP knock-out (PLTP0) mice[15] show that PLTP mediates the transfer of phospholipids from the apolipoprotein B-containing lipoprotein (BLp) into HDL, and demonstrate the importance of this process in the maintenance of HDL levels. However, a role of PLTP in the metabolism of BLp per se has not been previously considered. The present application discloses that PLTP deficiency has a major effect on the hepatic secretion of BLp, resulting in reduced BLp levels.

SUMMARY OF THE INVENTION

This invention is directed to a method of decreasing apolipoprotein B-containing lipoprotein or triglyceride in a subject which comprises administering to the subject an amount of a compound effective to decrease plasma phospholipid transfer protein activity and thereby decrease apolipoprotein B-containing lipoprotein or triglyceride.

This invention provides a method of treating dyslipidemia or cardiovascular disease in a subject which comprises administering to the subject an amount of a compound effective to decrease plasma phospholipid transfer protein activity and thereby treat the subject's dyslipidemia or cardiovascular disease.

The invention provides a method of identifying a chemical compound which decreases apolipoprotein B-containing lipoprotein or triglyceride, which comprises contacting cells expressing plasma phospholipid transfer protein (PLTP), or contacting an extract from said cells, with the chemical compound under conditions suitable for decreasing PLTP activity, and detecting a decrease in PLTP activity in the presence of the chemical compound so as to thereby identify the chemical compound as a compound which decreases apolipoprotein B-containing lipoprotein or triglyceride, wherein a decrease in PLTP activity results in decreased apolipoprotein B-containing lipoprotein or triglyceride.

The invention provides a method of screening a plurality of chemical compounds not known to decrease apolipoprotein B-containing lipoprotein or triglyceride to identify a chemical compound which decreases apolipoprotein B-containing lipoprotein or triglyceride, which comprises:

(a) contacting cells expressing plasma phospholipid transfer protein (PLTP), or contacting an extract from said cells, with the plurality of chemical compounds under conditions suitable for decreasing PLTP activity;

(b) determining if PLTP activity is decreased in the presence of the plurality of chemical compounds; and, if so, (c) separately determining if PLTP activity is decreased in the presence of each compound included in the plurality of chemical compounds, so as to thereby identify any compound included therein as a compound which decreases apolipoprotein B-containing lipoprotein or triglyceride, wherein a decrease in PLTP activity results in decreased apolipoprotein B-containing lipoprotein or triglyceride.

The invention provides a method of identifying a chemical compound for treating dyslipidemia or cardiovascular disease, which comprises contacting cells expressing plasma phospholipid transfer protein (PLTP), or contacting an extract from said cells, with the chemical compound under conditions suitable for decreasing PLTP activity, and detecting a decrease in PLTP activity in the presence of the chemical compound so as to thereby identify the chemical compound as a compound for treating dyslipidemia or cardiovascular disease, wherein a decrease in PLTP activity is effective to treat dyslipidemia or cardiovascular disease.

The invention provides a method of screening a plurality of chemical compounds not known to treat dyslipidemia or cardiovascular disease to identify a chemical compound for treating dyslipidemia or cardiovascular disease, which comprises:

(a) contacting cells expressing plasma phospholipid transfer protein (PLTP), or contacting an extract from said cells, with the plurality of chemical compounds under conditions suitable for decreasing PLTP activity;

(b) determining if PLTP activity is decreased in the presence of the plurality of chemical compounds; and, if so, (c) separately determining if PLTP activity is decreased in the presence of each compound included in the plurality of chemical compounds, so as to thereby identify any compound included therein as a compound for treating dyslipidemia or cardiovascular disease, wherein a decrease in PLTP activity is effective to treat dyslipidemia or cardiovascular disease.

The invention provides a compound identified by any of the methods disclosed herein.

The invention provides a pharmaceutical composition comprising (a) an amount of a chemical compound identified using any of the methods disclosed herein, or a novel structural and functional homolog or analog thereof, effective to reduce PLTP activity and (b) a pharmaceutically acceptable carrier.

The invention provides a method for preparing a composition which comprises admixing a carrier and a pharmaceutically effective amount of a chemical compound identified by any of the methods disclosed herein or a novel structural and functional analog or homolog thereof.

The invention provides a method for making a composition of matter which decreases apolipoprotein B-containing lipoprotein or triglyceride, which comprises identifying a chemical compound using any of the methods disclosed herein, and then synthesizing the chemical compound or a novel structural and functional analog or homolog thereof.

The invention provides a method for making a composition of matter for treating dyslipidemia or cardiovascular disease which comprises identifying a chemical compound using any of the methods disclosed herein, and then synthesizing the chemical compound or a novel structural and functional analog or homolog thereof.

The invention provides a method of treating a subject with elevated apolipoprotein B-containing lipoprotein or elevated triglyceride, which comprises administering to the subject a therapeutically effective amount of a chemical compound identified by any of the methods disclosed herein, or a novel structural and functional analog or homolog thereof.

The invention provides a method of treating a subject with dyslipidemia or cardiovascular disease which comprises administering to the subject a therapeutically effective amount of a chemical compound identified by any of the methods disclosed herein, or a novel structural and functional analog or homolog thereof.

The invention provides a use of a chemical compound identified by any of the methods disclosed herein for the preparation of a pharmaceutical composition for treating an abnormality, wherein the abnormality is alleviated by decreasing plasma phospholipid transfer protein activity.

Figure 1:
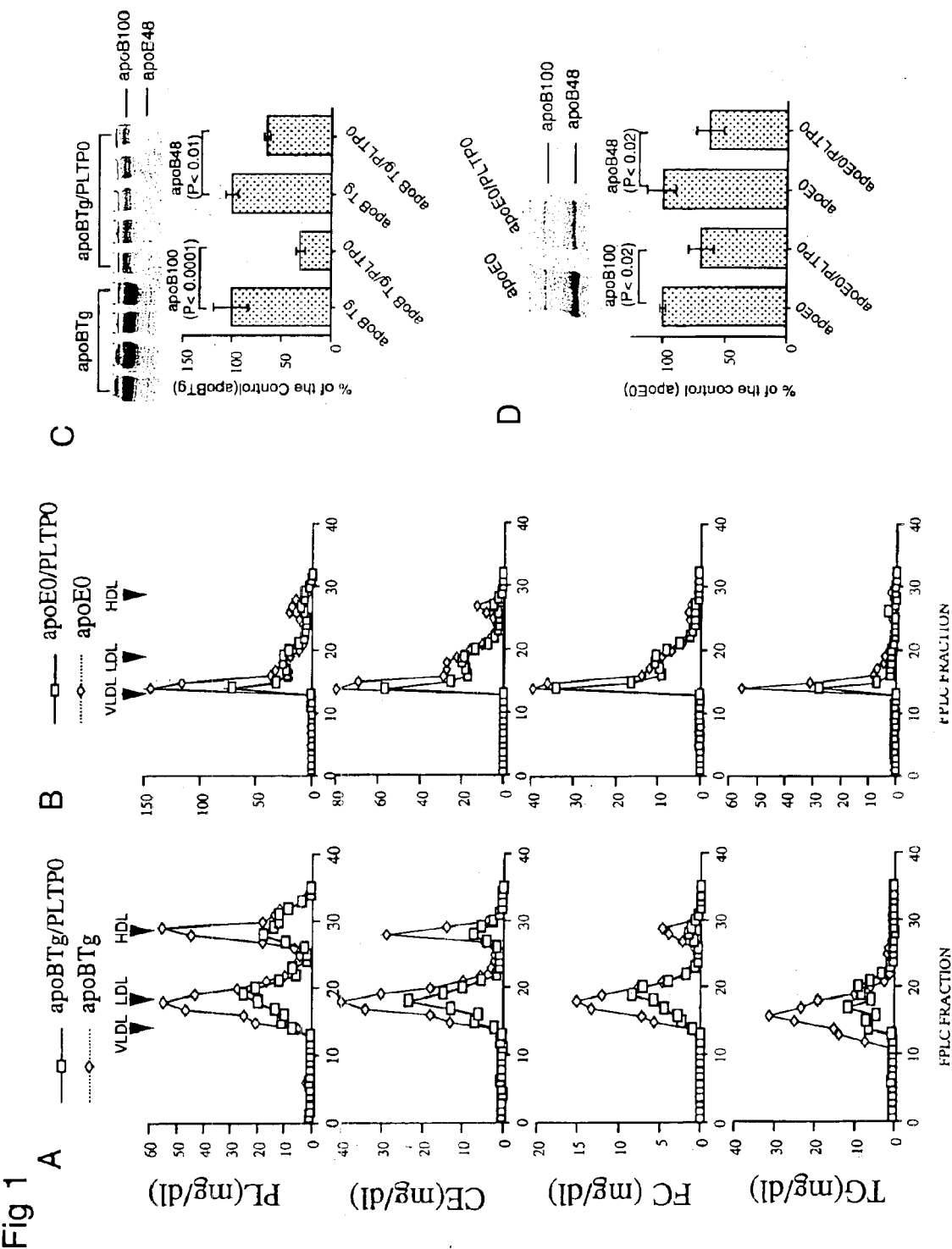
FIGS. 1A–D

A and B, Plasma lipoprotein analysis by fast protein liquid chromatography (FPLC). Pooled mouse plasma (200 µl) was used for FPLC. An aliquot of each fraction was used for the determination of free cholesterol, cholesteryl ester, phospholipid and triglyceride.

C and D, SDS-PAGE analysis of apoB from ultracentrifugally isolated plasma lipoproteins. The relative abundance of the apoB100 and apoB48 was calculated by quantitative scanning (Kodak Digital Science, ID Image Analysis Software). (n=6 for each genotype).

FIGS. 2A–F

A, Radioactivity decay curves for $^{125}$I-LDL in apoBTg and apoBTg/PLTP0 mice. B, apoB production rate measurement in apoBTg and apoBTg/PLTP0 mice; C, radioactivity decay curves for $^3$H-PC-VLDL in apoBTg and apoBTg/PLTP0 mice; D, apoB production rate measurement in apoE0 and apoE0/PLTP0 mice; E, apoB production rate measurement in wild type and PLTP0 mice; and F, apoB production rate measurement in LDLr0 and LDLr0/PLTP0 mice.

FIGS. 3A–E

Primary hepatocyte culture, immunoprecipitation and analysis of apoB or albumin from culture medium or cel lysate were performed as described previously[18]. A, pulse change experiment, apoB in the cell media; B, pulse chase experiment, apoB in the cell lysate; C, determination of apoB secretion rate in the presence and absence of the proteoscfial inhibitor ALLN. Hepatocytes from apoBTg/PLTP0 and apoBTg mice were radiolabeled continuously with $^{35}$Smethionine/cystein with or without 40 µg/ml ALLN fcr 30 mm. Cells ware lysed and lysates immunoprecipitated with apoB antibody. Samples were separated on SDS PAGE. D, determination of apoB secretion rate in the presence and absence of heparin. Hepatocytes from apoBTG/PLTP0 and apoBTg mice were radiolabeled continuously with $^{35}$Smethionine/cystein with or without 10 mg/ml heparin for 3 hr. Media immunoprecipitated with apoB antibody. Samples were separated on SDS PAGE. E, PLTP activity exists in secretory pathway. Hepatocyte (from Wt and PLJTP0 mice) fractions were collected and ruptured. The resulting solutions were trised for PLTP activity assay[15] and total protein concentratio measurement. Western blot was performed using anti-Golgi 58K protein polyclonal antibody as a Golgi complex marker, and using anti-protein disulfide isomerase antibody as an endoplasmic reticulum marker.

FIGS. 4A–C

Determination of apoB secretion after adenovirus-mediated overexpression of the human PLTP. ApoBTg/PLTP0 and LDLr0/PLTP0 hepatocytes were infected with adenovirus containing either the PLTP gene, or the gene encoding a green fluorescent protein (GFP). A, PLTP activity in cell media with Adv-PLTP or Adv-GFP infection. B, ApoB secretion from apoBTg/PLTP0 mouse hepatocytes with Adv-PLTP or Adv-GFP infection. C, ApoB secretion from LDLr0/PLTP0 mouse hepatocytes with Adv-PLTP or Adv-GFP infection.

FIGS. 5A–C

Extent of atherosclerosis in the proximal aorta of mice. A, three months old apoBTg and apoBTg/PLTP0 mice were fed a Western type diet for 6 months, then sacrificed for the study. B, Three months old of apoE0 and apoE0/PLTP0 (on chow) were sacrifice for the study. C, three months old LDLr0 and LDLr0/PLTP0 mice were on a Western type diet for 3 months, then sacrificed for the study.

DETAILED DESCRIPTION OF THE INVENTION

The following definitions are presented as an aid in understanding this invention:

ApoB—apolipoprotein B;
ApoBTg—human apoB transgenic mice;
ApoE—apolipoprotein E;
ApoE0—apolipoprotein E knock-out strain mice;
BLp—apoB containing lipoprotein;
CETP—cholesteryl ester transfer protein;
HDL—high density lipoprotein;
IDL—intermediate density lipoprotein;
LDL—low density lipoprotein;
LDLr—low density lipoprotein receptor;
LDLr0—LDL receptor knock-out strain mice;
MTP—microsomal triglyceride transfer protein;
PLTP—plasma phospholipid transfer protein;

PLTP0—PLTP knock-out strain mice;
VLDL—very low density lipoprotein.

Having due regard to the preceding definitions, this invention is directed to a method of decreasing apolipoprotein B-containing lipoprotein or triglyceride in a subject which comprises administering to the subject an amount of a compound effective to decrease plasma phospholipid transfer protein activity and thereby decrease apolipoprotein B-containing lipoprotein or triglyceride. In one embodiment, the decrease in apolipoprotein B-containing lipoprotein requires low density lipoprotein receptor activity.

This invention provides a method of treating dyslipidemia or cardiovascular disease in a subject which comprises administering to the subject an amount of a compound effective to decrease plasma phospholipid transfer protein activity and thereby treat the subject's dyslipidemia or cardiovascular disease.

In different embodiments of any of the methods disclosed herein, the dyslipidemia occurs in familial hyperlipidemia, obesity, or diabetes. In one embodiment of any of the methods disclosed herein, the cardiovascular disease is atherosclerosis.

In one embodiment of any of the methods disclosed herein, the compound which decreases plasma phospholipid transfer protein activity also decreases cholesteryl ester transfer protein activity.

In one embodiment of any of the methods disclosed herein, the compound which decreases plasma phospholipid transfer protein activity also increases high density lipoprotein.

In different embodiments of the methods described herein, plasma phospholipid transfer protein activity is decreased by pharmacological techniques, recombinant techniques, or gene therapy techniques.

The invention provides a method of identifying a chemical compound which decreases apolipoprotein B-containing lipoprotein or triglyceride, which comprises contacting cells expressing plasma phospholipid transfer protein (PLTP), or contacting an extract from said cells, with the chemical compound under conditions suitable for decreasing PLTP activity, and detecting a decrease in PLTP activity in the presence of the chemical compound so as to thereby identify the chemical compound as a compound which decreases apolipoprotein B-containing lipoprotein or triglyceride, wherein a decrease in PLTP activity results in decreased apolipoprotein B-containing lipoprotein or triglyceride. In one embodiment, the chemical compound is not previously known to decrease apolipoprotein B-containing lipoprotein or triglyceride.

The invention provides a method of screening a plurality of chemical compounds not known to decrease apolipoprotein B-containing lipoprotein or triglyceride to identify a chemical compound which decreases apolipoprotein B-containing lipoprotein or triglyceride, which comprises:
(a) contacting cells expressing plasma phospholipid transfer protein (PLTP), or contacting an extract from said cells, with the plurality of chemical compounds under conditions suitable for decreasing PLTP activity;
(b) determining if PLTP activity is decreased in the presence of the plurality of chemical compounds; and, if so,
(c) separately determining if PLTP activity is decreased in the presence of each compound included in the plurality of chemical compounds, so as to thereby identify any compound included therein as a compound which decreases apolipoprotein B-containing lipoprotein or triglyceride, wherein a decrease in PLTP activity results in decreased apolipoprotein B-containing lipoprotein or triglyceride.

The invention provides a method of identifying a chemical compound for treating dyslipidemia or cardiovascular disease, which comprises contacting cells expressing plasma phospholipid transfer protein (PLTP), or contacting an extract from said cells, with the chemical compound under conditions suitable for decreasing PLTP activity, and detecting a decrease in PLTP activity in the presence of the chemical compound so as to thereby identify the chemical compound as a compound for treating dyslipidemia or cardiovascular disease, wherein a decrease in PLTP activity is effective to treat dyslipidemia or cardiovascular disease. In one embodiment, the chemical compound is not previously known to treat dyslipidemia or cardiovascular disease.

The invention provides a method of screening a plurality of chemical compounds not known to treat dyslipidemia or cardiovascular disease to identify a chemical compound for treating dyslipidemia or cardiovascular disease, which comprises:
(a) contacting cells expressing plasma phospholipid transfer protein (PLTP), or contacting an extract from said cells, with the plurality of chemical compounds under conditions suitable for decreasing PLTP activity;
(b) determining if PLTP activity is decreased in the presence of the plurality of chemical compounds; and, if so,
(c) separately determining if PLTP activity is decreased in the presence of each compound included in the plurality of chemical compounds, so as to thereby identify any compound included therein as a compound for treating dyslipidemia or cardiovascular disease, wherein a decrease in PLTP activity is effective to treat dyslipidemia or cardiovascular disease.

In different embodiments of any of the methods disclosed herein, the dyslipidemia occurs in familial hyperlipidemia, obesity, or diabetes. In one embodiment of any of the methods disclosed herein, the cardiovascular disease is atherosclerosis.

In one embodiment of any of the methods disclosed herein, the compound which decrease plasma phospholipid transfer protein (PLTP) activity also decreases cholesteryl ester transfer protein activity.

In one embodiment of any of the methods disclosed herein, the compound which decrease plasma phospholipid transfer protein (PLTP) activity also increases high density lipoprotein.

In one embodiment, PLTP is measured in the cell medium.
In one embodiment, PLTP is measured by measuring the messenger ribonucleic acid (mRNA) that encodes PLTP.

In different embodiments of any of the methods disclosed herein, the cells are liver cells or liver cancer cells. In different embodiments, the liver cancer cells are human liver cancer cells or rat liver cancer cells. In one embodiment, the human liver cancer cells are HepG2 cells. In one embodiment, the rat liver cancer cells are AcARH7777 cells. In one embodiment, the cells are vertebrate cells. In one embodiment, the vertebrate cells are mammalian cells. In one embodiment, the mammalian cells are human cells. In one embodiment, the cells express apolipoprotein B.

In one embodiment, the cells do not normally express plasma phospholipid transfer protein (PLTP) and nucleic acid encoding PLTP is transfected into the cells. In different embodiments, the cells are yeast, fungal, insect, vertebrate, or mammalian cells. In further embodiments, the mammalian cells are HEK293 cells, Chinese hamster ovary (CHO)

cells, COS-7 cells, LM(tk-) cells, mouse embryonic fibroblast NIH-3T3 cells, mouse Y1 cells, 293 human embryonic kidney cells, or HeLa cells. In further embodiments, the insect cells are Sf9 cells, Sf21 cells or *Trichoplusia* ni 5B-4 cells. In one embodiment, the cells express apolipoprotein B.

Methods of transfecting cells with nucleic acid to obtain cells in which the encoded protein is expressed are well known in the art. Deoxyribonucleic acid (DNA) encoding proteins to be studied can be transiently expressed in a variety of cells lines by several transfection methods including but not limited to: calcium phosphate-mediated, DEAE-dextran mediated; liposomal-mediated, viral-mediated, electroporation-mediated, and microinjection delivery. Each of these methods may require optimization of assorted experimental parameters depending on the DNA, cell line, and the type of assay to be subsequently employed.

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin.

The invention provides a compound identified by any of the methods disclosed herein.

The invention provides a pharmaceutical composition comprising (a) an amount of a chemical compound identified using any of the methods disclosed herein, or a novel structural and functional homolog or analog thereof, effective to reduce PLTP activity and (b) a pharmaceutically acceptable carrier. In one embodiment, the compound is effective to decrease cholesteryl ester transfer protein activity.

The invention provides a method of preparing a composition which comprises identifying a chemical compound which decreases apolipoprotein B-containing lipoprotein or triglyceride using any of the methods disclosed herein and admixing the identified chemical compound with a carrier.

The invention provides a method of preparing a composition which comprises identifying a chemical compound for treating dyslipidemia or cardiovascular disease using any of the methods disclosed herein and admixing the identified chemical compound with a carrier.

The invention provides a method of preparing a composition which comprises identifying a chemical compound which decreases apolipoprotein B-containing lipoprotein or triglyceride using any of the methods disclosed herein, separating the compound from the cells or from an extract from the cells, and admixing the identified chemical compound with a carrier.

The invention provides a method of preparing a composition which comprises identifying a chemical compound for treating dyslipidemia or cardiovascular disease using any of the methods disclosed herein, separating the compound from the cells or from an extract from the cells, and admixing the identified chemical compound with a carrier.

The invention provides a method for preparing a composition which comprises admixing a carrier and a pharmaceutically effective amount of a chemical compound identified by any of the methods disclosed herein or a novel structural and functional analog or homolog thereof.

A "structural and functional analog" of a chemical compound has a structure similar to that of the compound but differing from it in respect to a certain component or components. A "structural and functional homolog" of a chemical compound is one of a series of compounds each of which is formed from the one before it by the addition of a constant element. The term "analog" is broader than and encompasses the term "homolog".

The invention provides a method for making a composition of matter which decreases apolipoprotein B-containing lipoprotein or triglyceride, which comprises identifying a chemical compound using any of the methods disclosed herein, and then synthesizing the chemical compound or a novel structural and functional analog or homolog thereof.

The invention provides a method for making a composition of matter for treating dyslipidemia or cardiovascular disease which comprises identifying a chemical compound using any of the methods disclosed herein, and then synthesizing the chemical compound or a novel structural and functional analog or homolog thereof.

The invention provides a method of treating a subject with elevated apolipoprotein B-containing lipoprotein or elevated triglyceride, which comprises administering to the subject a therapeutically effective amount of a chemical compound identified by any of the methods disclosed herein, or a novel structural and functional analog or homolog thereof.

The invention provides a method of treating a subject with dyslipidemia or cardiovascular disease which comprises administering to the subject a therapeutically effective amount of a chemical compound identified by any of the methods disclosed herein, or a novel structural and functional analog or homolog thereof. In different embodiments, the dyslipidemia occurs in familial hyperlipidemia, obesity or diabetes. In one embodiment, the cardiovascular disease is atherosclerosis.

The invention provides a use of a chemical compound identified by any of the methods disclosed herein for the preparation of a pharmaceutical composition for treating an abnormality, wherein the abnormality is alleviated by decreasing plasma phospholipid transfer protein activity. In different embodiments, the abnormality is elevated apolipoprotein B-containing lipoprotein, elevated triglyceride, dyslipidemia, or cardiovascular disease. In different embodiments, the dyslipidemia occurs in familial hyperlipidemia, obesity or diabetes. In one embodiment, the cardiovascular disease is atherosclerosis.

In the subject invention, a "pharmaceutically effective amount" is any amount of a compound which, when administered to a subject suffering from a disease against which the compound is effective, causes reduction, remission, or regression of the disease. Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

The following Experimental Details are set forth to aid in an understanding of the invention, and are not intended, and should not be construed, to limit in any way the invention set forth in the claims which follow thereafter.

EXPERIMENTAL DETAILS

Materials and Methods

Knock-out animals and diets: The PLTP knock-out trait was introduced into three different mutant strains. To achieve this, the PLTP knock-out trait was first back-crossed into the C57BL/6 background, and then intercrossed with human apoB transgenic mice[16], apoE knock-out mice[19] or LDL receptor knock-out mice[22], each in the C57BL/6 background. All phenotypic characterization were performed by comparison of litter mates. Two diets were used: Chow diet, and chow diet plus 20% milk fat and 0.15% cholesterol ("Western diet") (Teklad Premier Laboratory Diets, Madison, Wis.).

Lipids, lipoprotein and apolipoprotein measurements: Blood from fasted subjects was collected for lipoprotein isolation and lipid measurement (food was removed at 9:00 am and blood was collected at 4:00 pm). Total cholesterol, free cholesterol (FC) and phospholipid (PL) in plasma and lipoproteins were assayed by enzymatic methods (Wako Pure Chemical Industries Ltd., Osaka, Japan). Cholesteryl ester concentration was calculated by subtracting the amount of free cholesterol from the total plasma cholesterol. Lipoprotein profiles were obtained by means of fast protein liquid chromatography (FPLC) using a Sepharose 6B column as described previously[15]. A 200 µl aliquot of pooled plasma (from 7 animals) was loaded onto the column, and eluted with TS buffer (50 mM Tris, 0.15 M NaCl, pH 7.5) at a constant flow rate of 0.35 ml/min. An aliquot of 80 µl from each fraction (1 ml) was used for the determination of total cholesterol and phospholipid. To analyze the apolipoprotein composition, the ultracentrifugally isolated plasma lipoproteins (VLDL/LDL, d=1.006–1.063 g/ml, and HDL d=1.063–1.21 g/ml) were run on a 4–20% gradient sodium dodecyl sulfate-polyacrylamide gel electrophoresis (SDS-PAGE) gel under reducing condition. The apolipoproteins then were stained by Coomassie brilliant blue. Apolipoprotein was quantitated by gel scanning software (NIH Image).

In vivo turnover study: Autologous mouse LDL or human LDL was labeled with $^{125}$I (Pierce Chemical Company, Rockford, Ill.) as described previously[39]. [$^{125}$I]-LDL (2×10$^7$ cpm) were injected intravenously into the apoBTg/PLTP0 and apoBTg mice. Following injection, blood (70 µl) was taken from the tail vein at 0, 10, 20, 30, 40, and 60 minutes. The fractional catabolic rate (FCR) for protein and FC was calculated from the decay curve of [$^{125}$I]-LDL radioactivity in whole plasma according to the Matthews method[40].

Primary hepatocyte culture: Hepatocytes were isolated according to the method described previously[41] with the modification that complete protease inhibitor was added to digestion buffer according to the manufacturer's instructions (Boehringer Mannheim Biochemicals, Mannheim, Germany).

Immunoprecipitation and analysis of apoB from culture medium or cell lysate: The primary hepatocytes were allowed to attach to dishes for 90 minutes. Hepatocytes were incubated for 1 hour in starvation medium (methionine/cysteine-free Dulbecco Modified Eagle Medium (DMEM) supplemented with 0.2 mM oleic acid (conjugated to bovine serum albumin (BSA))) before pulse labeling for 15 minutes with tracer (50 µl [$^{35}$S]methionine/cysteine (Pro-mix, 530 Mbq/ml, Amersham Pharmacia Biotech) per ml of medium). Dishes were washed once with DMEM before addition of chase medium (DMEM supplemented with 10 mM each of unlabeled methionine and cysteine and 0.2 mM oleic acid). At each chase time point (30 minutes, 1 hour and 2 hours), medium apoB and cell lysate apoB were immunoprecipitated by apoB antibody together with protein A/G agarose, the precipitates were size-fractionated on a 4% SDS PAGE gel, the gel was dried, and the incorporation of $^{35}$S into apoB48 and apoB100 was assessed with a Fuji Bio-Imaging Analyzer (Fuji Medical Systems, Stamford, Conn.).

Mouse apoB production rate measurement: The procedure was described previously[22]. Briefly, apoBTTg/PLTP0 and apoBTg mice were injected with [$^{35}$S]-methionine to label apoB, and with Triton WR1339 to block the clearance of nascent BLp from the circulation. The labeled apoB48 and apoB100 were separated on 4% SDS PAGE and the incorporation of $^{35}$S into apoB48 and apoB100 was assessed with a Fuji Bio-Imaging Analyzer (Fuji Medical Systems, Stamford, Conn.).

Hepatocyte fractionation and PLTP activity measurement: The primary hepatocytes were homogenized by passage through a ball bearing homogenizer (Industrial Techtonics, Inc) 10 times. The homogenate was centrifuged at 1,900 g for 10 minutes at 4° C. The supernatant was collected and adjusted to 0.5% bovine serum albumin (BSA) and layered on top of a sucrose gradient (20%–56%). The solution was centrifuged at 38,000 rpm, 4° C. for 15 hours. Fractions were collected from the top to the bottom, each fraction was 10 times diluted with phosphate buffered saline (PBS) and concentrated at 38,000 rpm, 4° C. for 1 hour. Each pellet was resuspended in PBS and sonicated. The resulting solutions were used for PLTP activity assay[15] and total protein concentration measurement. Western blot was performed using anti-Golgi 58K protein polyclonal antibody (Sigma) as a Golgi complex marker, and using anti-protein disulfide isomerase antibody (Stressgen Biotechnologies Corp) as an endoplasmic reticulum marker.

PLTP activity assays: Egg phosphatidylcholine (10 µmol) containing 10 nmol of [3H]PC (L-a-dipalmitoyl-[2-palmitoyl-9,10-3H(N)]-phosphatidylcholine) was dried under a stream of nitrogen, resuspended in 1 ml of a solution of 10 mM Tris, 150 mM NaCl, 1 mM ethylenediaminetetraacetic acid (EDTA) (pH 7.4), and then probe-sonicated and centrifuged. Transfer of radiolabeled phospholipid was measured by incubating 3 µl of plasma with radiolabeled phospholipid vesicles (125 nmol PC) and HDL (250 µg protein) in a final volume of 400 µl at 37° C. for 1 hour.

PLTP inhibition assay:
The following compound, which is a known cholesteryl ester transfer protein (CETP) inhibitor (compound No. 3 in Okamoto et al.[38]) was dissolved in dimethlysulfonyl oxide (DMSO) (stock solution 2 mM):

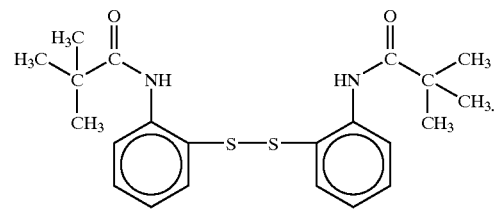

A final volume of 400 µl assay system was prepared containing phosphatidylcholine, HDL, 3 µl of plasma, and 0–50 µM of the compound. Vesicles were subsequently precipitated by the addition of 300 µl of a solution of 500 mM NaCl, 215 mM MnCl$_2$, 445 U/ml heparin, and the radioactivity of a 500-µl aliquot of the supernatant was measured.

Determination of apoB secretion after adenovirus-mediated overexpression of the human PLTP: The Adv-PLTP (E1, E3 deleted) was made using the AdEasy system kindly provided by Dr. Tong-Chuan He. Briefly, an EcoRI-KpnI fragment containing the PLTP cDNA, derived from plasmid BSKS-RSV-PLTP, was inserted into a pShuttle plasmid containing the CMV promoter. To generate the recombinant adenoviral plasmid, PmeI linearized pShuttle-CMV-PLTP vector and supercoiled pAd-Easy-1 were co-transformed into *E. coli* BJ5183. The recombinant Adv-PLTP plasmid was examined by restriction endonuclease digestions. To generate the adenoviral vector, Adv-PLTP was transfected into 293 cells by calcium phosphate transfection methods. The Adv-PLTP virus was propagated and purified as described in the AdEasy system[42]. The control Adv-GFP vector containing the green fluorescent protein gene under the control of CMV promoter was plaque purified and amplified on 293 cells[43]. After two rounds of purification by CsCl ultra-centrifugation, the adenoviral vector titers were determined by viral genome particle numbers. Approximately fifty viral genome particles gave rise to one plaque forming units (pfu). $1 \times 10^8$ pfu/ml was used to infect one well cell (six well plate).

Extent of atherosclerosis in the proximal aorta of mice: Mice were sacrificed, and the heart and proximal aorta were removed. The hearts were stored in 10% formalin at 4° C. before sectioning. Sequential sections 10 μm-thick were made with a cryostat and stained with Oil Red O. The mean area of red color lipid staining per section per animal from five sections was determined for each individual animal. The statistical significance of the differences between the groups was estimated by the Student's t-test.

PLTP Deficiency Decreases BLp Levels in apoB Transgenic and apoE Knock-out Mice But Not in LDL Receptor Knock-out Mice Human apoBTg transgenic mice synthesize apoB in the liver[16], have similar plasma apoB levels to humans and develop atherosclerosis when fed a high fat/cholesterol diet[17]. PLTP deficiency results in a marked reduction in the levels of BLp, with decreased levels of cholesterol esters (31%), free cholesterol (47%), phospholipids (44%) and triglycerides (61%) in VLDL/LDL (or non-HDL), compared to controls (FIG. 1A, Table 1). There was a dramatic 66% decrease in apoB100 (p<0.0001), the major form of apoB in plasma, and a 25% decrease in apoB48 (p<0.01), in VLDL/LDL from apoBTg/PLTP0 mice compared to that from apoBTg mice (FIG. 1C). HDL levels were reduced in PLTP0 mice (FIG. 1A). These findings show that PLTP has a major role in determining not only the HDL concentration, but also the levels of BLp in plasma.

The PLTP deficiency trait was also crossed into the apoE0 knock-out background. ApoE is carried on VLDL and IDL and mediates receptor-mediated clearance of these particles in the liver[18]. ApoE0 mice develop marked hypercholesterolemia on a chow diet, as a result of defective clearance of BLp[19,20]. The predominant accumulating lipoprotein is an apoB48-containing, cholesterol ester rich particle that represents a remnant of intestinal chylomicrons[21]. When studied on a chow diet, apoE0/PLTP0 mice showed substantial reductions in phospholipid (42%), cholesterol esters (44%), free cholesterol (17%) and triglycerides (43%) in VLDL/LDL (Table 1, FIG. 1B). ApoB48 and apoB100 on VLDL/LDL were also decreased by 40% and 31%, respectively, compared to apoE0 controls (FIG. 1D). These studies reveal a previously unknown role of PLTP in determining the plasma levels of BLp in both apoBTg and apoE0 mice.

A strikingly different result was obtained when the PLTP deficiency trait was crossed into the LDLr0 knock-out background. LDLr0 mice accumulate IDL and LDL, as a result of impaired LDL receptor-mediated clearance of BLp in the liver[22]. Although HDL levels were significantly decreased in LDLr0/PLTP0 mice (Table 1), there was no alteration of the levels of BLp in the circulation (Table 1). Similar results were obtained by FPLC analysis. ApoB levels in VLDL/LDL were similar in LDLr0 mice versus LDLr0/PLTP0 mice: 100±18 vs 108±21 arbitrary units for apoB100; 100±15 vs 110±25 arbitrary units for apoB48, as determined by scanning SDS-PAGE gels, n=5 per group. These results indicate a role of the LDL receptor in reducing BLp levels in PLTP deficient mice.

PLTP Deficiency Decreases apoB Production Rate in apoBTg and apoE0 Mice but not in LDLr0 Mice In order to investigate the mechanisms responsible for the reduced BLp levels in PLTP0 mice, the possibility that remodeling of BLp by PLTP in the circulation results in more efficient clearance by the LDL receptor was investigated using LDL turnover experiments. After injection of [$^{125}$I]-LDL, there were superimposable decay curves (FIG. 2A), indicating identical catabolism of BLp. In vivo ApoB production rates were then examined. ApoBTg mice were injected with [$^{35}$S]-methionine to label apoB, and with Triton WR1339 to block the clearance of nascent BLp from the circulation[23]. This showed reduced production of both apoB100 and apoB48 (by 49% and 47%, respectively, n=5, p<0.01) in apoBTg/PLTP0 mice compared to apoBTg controls (FIG. 2B). Even though apoB clearance was unaffected, there was delayed clearance of surface phospholipid in VLDL injected into apoBTg/PLTP0 mice (FIG. 2C), presumably reflecting defective transfer into HDL[15]. Triton experiments also showed reduced production of both apoB100 and apoB48 (by 35% and 52%, p<0.05 and p<0.02, respectively, n=5) in apoE0/PLTP0 mice compared to apoE0 mice (FIG. 2D) and in PLTP0 compared to wild type mice (FIG. 2E) However, similar experiments in LDLr0 versus LDLr0/PLTP0 mice showed no difference in BLp production rates (n=5, FIG. 2F). These results show a major influence of PLTP on the production of BLp, both from the liver (apoBTg mouse) and small intestine (apoE0 mouse). A role of the LDL receptor in reducing BLp levels is indicated by the results in FIGS. 2E and 2F.

PLTP Deficiency Decreases apoB Secretion from Hepatocytes

Figure 3:
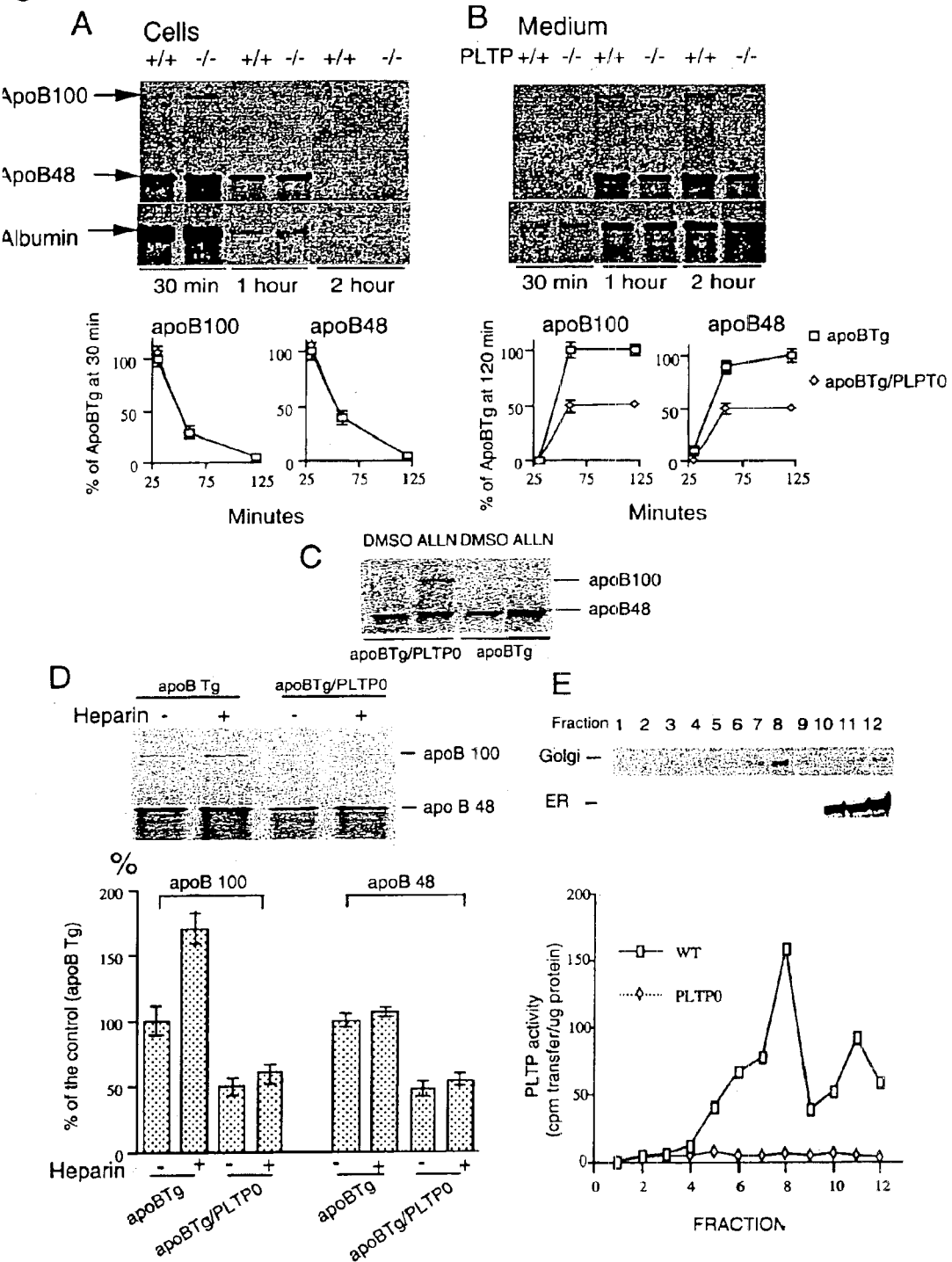

To examine the effect of PLTP deficiency on apoB secretion at a cellular level, metabolic labeling (pulse-chase) experiments were performed using primary hepatocytes derived from apoBTg mice. There was a marked reduction in secretion of apoB100 (by 55%, n=4, p<0.01) and a lesser reduction in secretion of apoB48 (by 42%, n=4, p<0.01) from hepatocytes of apoBTg/PLTP0 mice, compared to cells from apoBTg controls (FIG. 3B). In contrast, there was no difference in apoB accumulation within cells during the chase period (FIG. 3A), indicating that PLTP deficiency did not affect ApoB synthesis. Albumin synthesis and secretion were unaffected in PLTP0 hepatocytes. There was no difference in apoB accumulation in hepatocytes after 1 hour of chase (FIG. 3A). These results indicate decreased secretion of apoB in apoBTg/PLTP0 mice, which is associated with an increase in intracellular degradation. This was confirmed by inclusion of N-acetyl-leu-leu-norleu-AL (ALLN) (calpain inhibitor 1) in the incubation, which inhibits degradation of ApoB in proteasomes[24]. ALLN treatment resulted in increased levels of apoB within cells, especially PLTP deficient cells, consistent with decreased apoB secretion (FIG. 3C).

Instead of decreased secretion, an alternative explanation for these finding could be increased re-uptake from medium of newly secreted BLp in PLTP deficient hepatocytes. To test this possibility, the accumulation of BLp in media was determined in the presence of heparin, which blocks the re-uptake of BLp both by the LDL receptor and by proteoglycans. As expected[25,26], heparin increased the accumulation of BLp in media from apoB transgenic mice. However, heparin failed to increase BLp accumulation in media from PLTP deficient hepatocytes (FIG. 3D). This finding could arise if a subpopulation of VLDL, more susceptible to intracellular clearance by the LDL receptor[25], had already been removed before secretion. These findings indicate that PLTP deficiency does not lead to increased re-uptake of BLp from media into cells, and point to a possible role of PLTP in the assembly of BLp within the cell.

Previously, PLTP has only been considered to be active in plasma[27]. To see if PLTP might be active in intracellular sites, cellular organelles were isolated and ruptured. This resulted in release of abundant PLTP activity from the Golgi complex, with a lesser peak of activity in fractions enriched for endoplasmic reticulum markers (FIG. 3E). This activity was absent in organelles of PLTP0 mice (FIG. 3E), confirming specificity of the assay. These findings are consistent with the idea that PLTP may have a role in the biosynthesis of BLp, related to its activity in the Golgi complex or endoplasmic reticulum.

An alternative explanation for decreased secretion of BLp by hepatocytes from PLTP0 mice is that altered plasma lipoprotein metabolism in vivo secondarily changes hepatocyte lipid metabolism. To assess this possibility the PLTP gene was re-introduced into primary hepatocytes of apoBTg/PLTP0 mice by infection with adenovirus-PLTP. PLTP overexpression increased PLTP activity (to about 2.5 fold wild type levels) and apoB secretion (FIGS. 4A, B), whereas albumin was unaffected. In contrast, PLTP overexpression did not influence apoB secretion from LDLr0/PLTP0 mouse hepatocytes (FIG. 4C). These results show a direct effect of PLTP activity in hepatocytes to increase secretion of BLp. A similar effect is not observed in LDL receptor deficient hepatocytes. Restoration of PLTP activity back to wild type levels by injecting adenovirus associated virus-PLTP into PLTP0 mice led to significant increases in apoB levels, indicating that the effect of PLTP on apoB levels is independent of the presence of other transgenes.

To determine if the defect in secretion of BLp was accompanied by accumulation of lipid in the liver, hepatic triglyceride content was measured. However, this showed no alteration in triglyceride content (ApoE0 vs ApoE0/PLTP0, 9±3 mg/g liver vs 10±4 mg/g liver, n=5; ApoBTg vs ApoBTg/PLTP0, 12±2 mg/g liver vs 13±3 mg/g liver, n=5).

PLTP Deficiency Decreases Atherosclerosis

Figure 5:
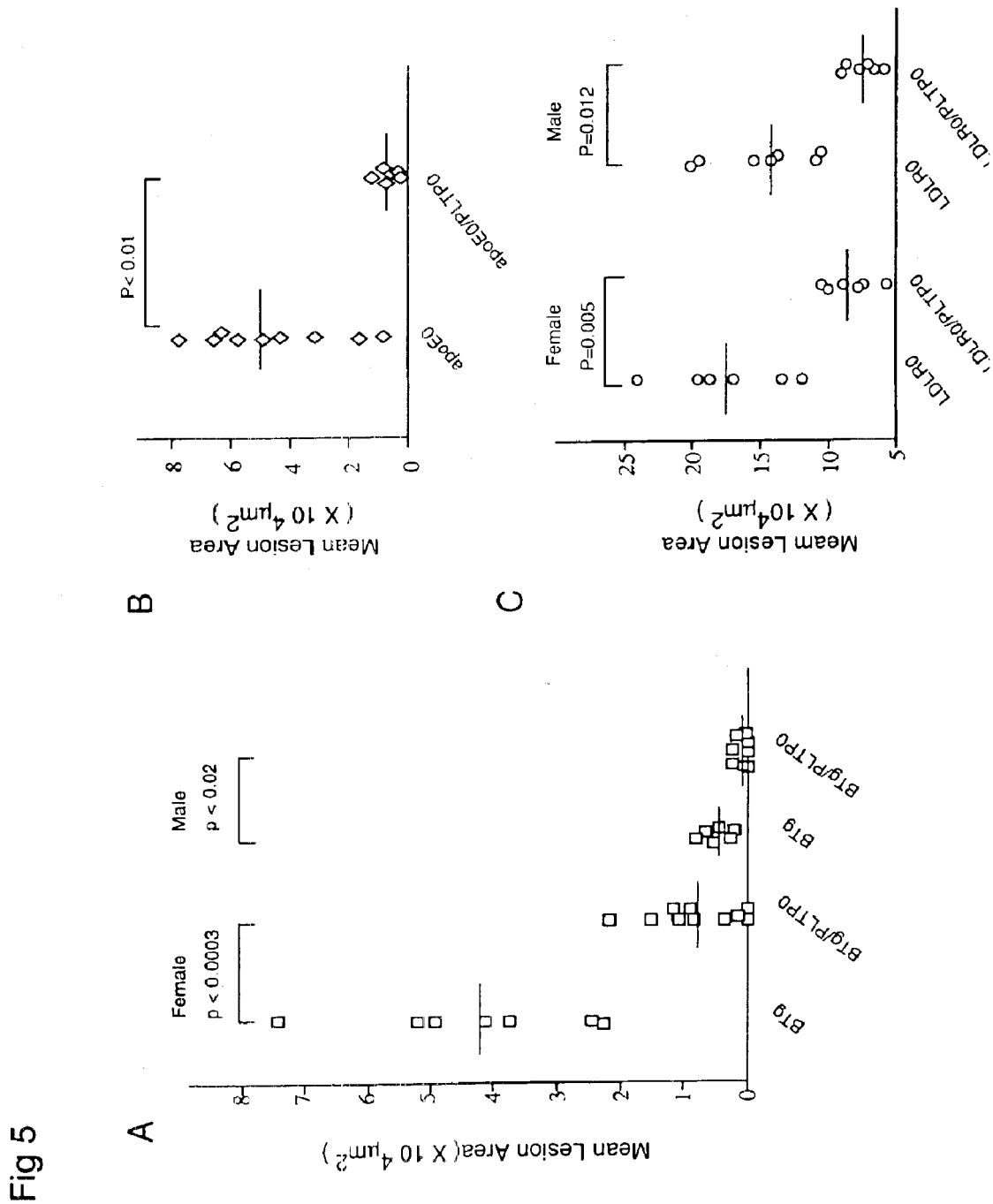

In order to evaluate the effect of PLTP deficiency on atherogenesis, proximal aortic lesion area was assessed in three models. ApoBTg and apoBTg/PLTP0 mice were fed the Western diet for 6 months. There was a profound 80% reduction in mean atherosclerotic lesion area in female apoBTg/PLTP0 mice, compared to apoBTg controls. Although lesions were much smaller in males, there was a similar 80% reduction in atherosclerosis in PLTP0 male mice (FIG. 5A). After 3 months on a chow diet, apoE0/PLTP0 males showed a 72% reduction in mean lesion area, compared to apoE0 controls (FIG. 5B). In contrast, male LDLr0/PLTP0 mice, on the Western diet for 12 weeks, showed no significant reduction in mean lesion area compared to LDLr0 controls. However, when fed the diet for a shorter period of time (8 weeks), there was a significant reduction in lesion area in LDLr0/PLTP0 mice, compared to LDLr0 controls (FIG. 5C). These results suggest that part of the anti-atherogenic effect of PLTP deficiency is related to reduced BLp production and levels. However, additional anti-atherogenic mechanisms are likely present, since LDLr0/PLTP0 mice did not show a significant reduction in early lesion development.

CETP/PLTP Inhibition

Cholesteryl ester transfer protein (CETP) mediates the exchange of cholesteryl ester in HDL for triglyceride in VLDL[44,45]. Inhibition of CETP decreases cholesterol and attenuates atherosclerosis in rabbits[38].

The present application discloses that a known CETP inhibitor (compound #3 in Okamoto et al.[38]) is also an inhibitor of PLTP, with a similar Ki for PLTP activity (15 $\mu$M) as reported for CETP activity (13 $\mu$M)[38]. Assays of PLTP activity and inhibition are described in the Materials and Methods section. Combined PLTP/CETP inhibition represents a novel opportunity to decrease BLp without production of fatty liver, while increasing HDL and decreasing atherosclerosis.

TABLE 1

Plasma lipid and lipoprotein analysis.

| Mice | Pasma PL | HDL PL | Non-HDL PL | Plasma Chol | HDL CE | HDL FC | NON-HDL CE | Non-HDL FC | Plasma TG |
|---|---|---|---|---|---|---|---|---|---|
| ApoBTg | 439 ± 59 | 168 ± 23 | 271 ± 36 | 316 ± 39 | 40 ± 16 | 15 ± 3 | 188 ± 27 | 73 ± 18 | 200 ± 55 |
| ApoBTg/PLTP0 | 222 ± 38 | 71 ± 12 | 151 ± 29 | 198 ± 49 | 19 ± 7 | 9 ± 3 | 131 ± 37 | 39 ± 8 | 77 ± 15 |
| P Value | <.001 | <.01 | <.01 | <01 | <.02 | <.05 | <.02 | <.01 | <.02 |
| ApoE0 | 250 ± 27 | 60 ± 9 | 190 ± 51 | 466 ± 39 | 41 ± 9 | 7 ± 4 | 275 ± 27 | 144 ± 15 | 71 ± 10 |
| ApoE0/PLTP0 | 153 ± 15 | 42 ± 11 | 111 ± 19 | 329 ± 26 | 30 ± 8 | 4 ± 1 | 175 ± 22 | 120 ± 12 | 40 ± 13 |
| P Value | <.001 | <.02 | <.01 | <.01 | <.05 | <.05 | <.01 | <05 | <.02 |
| LDLr0 | 613 ± 28 | 144 ± 19 | 469 ± 61 | 712 ± 64 | 70 ± 10 | 30 ± 4 | 351 ± 56 | 260 ± 36 | 338 ± 93 |
| LDLr0/PLTP0 | 592 ± 31 | 89 ± 12 | 503 ± 53 | 652 ± 79 | 34 ± 6 | 18 ± 3 | 298 ± 55 | 302 ± 49 | 291 ± 52 |
| P Value | NS | <.001 | NS | NS | <.01 | <.01 | NS | NS | NS |

ApoBTg and apoBTg/PLTP0 mice were on the Western diet (20% milk fat and 0.15% cholesterol). ApoE0 and apoE0/PLTP0 were on chow diet. LDLr0 and LDLr0/PLTP0 mice were on the Western diet. HDL was separated from Non-HDL by precipitation with HDL reagent (Sigma). The total cholesterol, free cholesterol, phospholipid and triglyceride concentrations were determined by enzymatic methods. Numbers of animals in each group are 5–6. PL, phospholipid; CE, cholesteryl ester; FC, free cholesterol; TG, triglyceride; Non-HDL, VLDL + LDL.

The regulation of the secretion of BLp is a topic of great importance, since increased secretion of BLp plays a major role in the dyslipidemia of familial combined hyperlipidemia, diabetes and obesity. The present application discloses a previously unsuspected role of PLTP in the secretion of BLp by the liver and the intestine. The finding of abundant PLTP activity in the Golgi complex suggests that PLTP has a role in the addition of lipid to developing BLp in this organelle. The biosynthesis of BLp is a two step process: initial lipidation of apoB occurs in the endoplasmic reticulum, and requires the activity of the microsomal triglyceride transfer protein. A poorly understood, slower second step probably involves the addition of further lipid to the nascent VLDL particle[28]. The Golgi complex is a significant site of phospholipid synthesis[29], and the present disclosure suggests that addition of such phospholipid to BLp could involve PLTP. Alternatively, PLTP could be involved in remodeling the lipoprotein surface in a way which facilitates secretion. Increased PLTP activity has been reported in type II diabetic subjects[9] and in obesity[10]. The present findings suggest a mechanistic link to explain the increased production of BLp in these conditions, i.e. increased PLTP activity results from hyperinsulinemia and leads to increased production of BLp in the liver.

An intriguing aspect of this study is the genetic evidence suggesting a link between the LDL receptor and PLTP activity in the secretion of BLp. LDL receptor deficiency appears to act as a suppressor mutation preventing the effect of PLTP deficiency on apoB secretion (Table 1, FIG. 4C). A number of different cellular mechanisms could be involved. For example, it has recently been suggested that the LDL receptor can act as a chaperone for nascent BLp within the secretory pathway. Overexpression of the LDL receptor decreases the secretion of BLp[25]. It is conceivable that the normal remodeling of nascent BLp by PLTP within the secretory pathway causes its release from the LDL receptor[25], leading to increased BLp secretion. However, additional mechanisms are likely to be involved, since PLTP deficiency led to reduced apoB48 production in apoE0 mice (FIG. 2D). Since apoB48 does not interact with the LDL receptor, this suggests an effect independent of the LDL receptor.

There is abundant evidence linking reduced levels of BLp to decreased atherosclerosis in mice[30], while effects of reduced HDL levels, as seen in PLTP0 mice, are inconsistent[31]. Thus, it is likely that a major anti-atherogenic mechanism in PLTP0 mice is related to decreased levels and production of BLp. However, an additional anti-atherogenic mechanism is suggested, because atherosclerosis was decreased in LDLr0/PLTP0 mice, without reduction in BLp production or levels. An intriguing possibility is that this is somehow related to delayed clearance of surface phospholipid from VLDL (FIG. 2C), even though this does not result in accumulation of excess vesicular material in plasma of Western diet fed animals (FIG. 1). Perhaps these "surface remnants" have anti-atherogenic properties related to reverse cholesterol transport, or competition with atherogenic particles in the arterial wall[32].

An important implication of the present findings is that PLTP may be a therapeutic target for the treatment of increased BLp levels and atherosclerosis. MTP inhibitors have also been proposed as drugs to decrease BLp secretion[33]. However, unlike MTP deficiency, in PLTP deficiency there is no accumulation of triglycerides in the liver. There are many differences in human and mouse lipoprotein metabolism, including the presence of an additional lipid transfer protein in human plasma, the cholesteryl ester transfer protein (CETP)[34]. CETP has also been widely considered as a therapeutic target, since human CETP deficiency results in markedly elevated HDL levels[35]. The CETP and PLTP structures are homologous and each has an N-terminal lipid binding pocket with a reactive cysteine in its base which is essential for function[36,37]. Combined inhibition of PLTP and CETP would result in both markedly reduced BLp, as well as increased HDL, producing a desirable, anti-atherogenic lipoprotein profile. Such a profile has, in fact, resulted from administration of anti-atherogenic CETP inhibitors, which react with a cysteine at the base of the N-terminal pocket[38]. The present application discloses that such inhibitors may be combined CETP/PLTP inhibitors, with a similar Ki for PLTP activity and CETP activity. Thus, combined PLTP/CETP inhibition may represent a novel way to decrease BLp levels without production of fatty liver, while increasing HDL and decreasing atherosclerosis.

REFERENCES

1. Young, S. G. Recent progress in understanding apolipoprotein B. *Circulation* 82, 1574–1594 (1990).
2. Havel, R. J. & Kane, J. P. In The Metabolic Basis of Inherited Disease. Scriver, C. R. Beaudet, A. R. Sly, W. S. Valle, D. Stanbury, J. B. Wyngaarden, J. B. & Frederickson, D. S. editors, McGraw-Hill, New York, 1129–1139 (1989).
3. Goldstein, J. L., & Brown, M. S. In The Metabolic Basis of Inherited Disease. C. R. Scriver, A. R. Beaudet, W. S. Sly, D. Valle, J. B. Stanbury, J. B. Wyngaarden and D. S. Frederickson, editors, McGraw-Hill, New York, 1215–1225 (1989).
4. Kane, J. P. & Havel R. J. In The Metabolic Basis of Inherited Disease. C. R. Scriver, A. R. Beaudet, W. S. Sly, D. Valle, J. B. Stanbury, J. B. Wyngaarden and D. S. Frederickson, editors, McGraw-Hill, New York, 1139–1150 (1989).
5. Chen, S. H. et al. Apolipoprotein B-48 is the product of a messenger RNA with an organ-specific in-frame stop codon. *Science* 238, 363–366 (1987).
6. Powell, L. M. et al. A novel form of tissue-specific RNA processing produces apolipoprotein-B48 in intestine. *Cell* 50, 831–840 (1987).
7. Goldstein, J. L. et al. Hyperlipidemia in coronary heart disease. II. Genetic analysis of lipid levels in 176 families and delineation of a new inherited disorder, combined hyperlipidemia. *J. Clin. Invest.* 52, 1544–1568 (1973).
8. Brunzell, J. D. et al. Plasma lipoproteins in familial combined hyperlipidemia and monogenic familial hypertriglyceridemia. *J. Lipid. Res.* 24, 147–155 (1983).
9. Duvillard, L. et al. Metabolic abnormalities of apolipoprotein B-containing lipoproteins in non-insulin-dependent diabetes: a stable isotope kinetic study. *Eur. J. Clin. Invest.* 30, 685–694 (2000).
10. Riches, F. M. et al. Hepatic secretion of very-low-density lipoprotein apolipoprotein B-100 studied with a stable isotope technique in men with visceral obesity. *Int. J. Obes. Relat. Metab. Disord.* 22, 414–423 (1998).
11. Ginsberg, H. N. Role of lipid synthesis, chaperone proteins and proteasomes in the assembly and secretion of apoprotein B-containing lipoproteins from cultured liver cells. *Clin. Exp. Pharmacol. Physiol.* 24, A29–32 (1997).
12. Wetterau, J. R. et al. Absence of microsomal triglyceride transfer protein in individuals with abetalipoproteinemia. *Science* 258, 999–1001 (1992).
13. Shoulders, C. C. et al. Abetalipoproteinemia is caused by defects of the gene encoding the 97 kDa subunit of a microsomal triglyceride transfer protein. *Hum. Mol. Genet.* 2, 2109–2116 (1993).
14. Havel, R. J., Kane, J. P. & Kashyap, M. L. Interchange of apolipoproteins between chylomicrons and high density lipoproteins during alimentary lipemia in man. *J. Clin. Invest.* 52, 32–38 (1973).
15. Jiang, X.-c. et al. Targeted mutation of plasma phospholipid transfer protein gene markedly reduces high-density lipoprotein levels. *J. Clin. Invest.* 103, 907–914 (1999).
16. Callow, M. J. Stoltzfus, L. J. Lawn, R. M. & Rubin, E. M. Expression of human apolipoprotein B and assembly of lipoprotein(a) in transgenic mice. *Proc. Natl. Acad. Sci. USA* 91, 2130–2134 (1994).
17. Veniant, M. M. et al. Susceptibility to atherosclerosis in mice expressing exclusively apolipoprotein B48 or apolipoprotein B100. *J. Clin. Invest.* 100, 180–188 (1997).
18. Mahley, R. W. Apolipoprotein E: cholesterol transport protein with expanding role in cell biology. *Science* 240, 622–630 (1988).

19. Plump, A. S. et al. Severe hypercholesterolemia in apolipoprotein E-deficient mice created by homologous recombination in ES cells. *Cell* 71, 343–353 (1992).
20. Zhang, S. H. et al. Spontaneous hypercholesterolemia and arterial lesions in mice lacking apolipoprotein E. *Science* 258, 468–471 (1992).
21. Plump, A. S. & Breslow, J. L. Apolipoprotein E and the apolipoprotein E-deficient mouse. *Annu. Rev. Nutr.* 15, 495–518 (1995).
22. Ishibashi, S. et al. Hypercholesterolemia in low density lipoprotein receptor knockout mice and its reversal by adenovirus-mediated gene delivery. *J. Clin. Invest.* 92, 883–893 (1992).
23. Aalto-Setala, K. et al. Mechanism of hypertriglyceridemia in human apoCIII transgenic mice: diminished VLDL fractional catabolic rate associated with increased apoCIII and reduced apoE on the particles. *J. Clin. Invest.* 90, 1889–1900 (1992).
24. Yeung, S. J., Chen, S. H. & Chan, L. Ubiquitin-proteasome pathway mediates intracellular degradation of apolipoprotein B. *Biochemistry* 35, 1343–1348 (1996).
25. Twisk, J. et al. The role of the LDL receptor in apolipoprotein B secretion. *J. Clin. Invest.* 105, 521–532 (2000).
26. Williams, K. J., Brocia, R. W. & Fisher, E. A. The unstirred water layer as a site of control of apolipoprotein B secretion. *J. Biol. Chem.* 265, 16741–16744 (1990).
27. Tall, A. R., Abreu, E. & Shuman, J. Separation of a plasma phospholipid transfer protein from cholesteryl ester/phospholipid exchange protein. *J. Biol. Chem.* 258, 2174–2180 (1983).
28. Hamilton, R. L. et al. Chylomicron-sized lipid particles are formed in the setting of apolipoprotein B deficiency. *J. Lipid Res.* 39, 1543–1557 (1998).
29. Fang, M., Rivas, M. P. & Bankaitis, V. A. The contribution of lipids and lipid metabolism to cellular functions of the Golgi complex. *Biochim. Biophys. Acta.* 1404, 85–100 (1998).
30. Veniant, M. M. et al. Insights into apolipoprotein B biology from transgenic and gene-targeted mice. *J. Nutr.* 129, 451S-455S (1999).
31. Zhang, S. H. et al. Paradoxical enhancement of atherosclerosis by probucol treatment in apolipoprotein E-deficient mice. *J. Clin. Invest.* 99, 2858–2866 (1997).
32. Williams, K. J. et al. Phospholipid liposomes acquire apolipoprotein E in atherogenic plasma and block cholesterol loading of cultured macrophages. *J. Clin. Invest.* 79, 1466–1472 (1987).
33. Wetterau, J. R. et al. An MTP inhibitor that normalizes atherogenic lipoprotein levels in WHHL rabbits. *Science* 282, 751–754 (1998).
34. Tall, A. R. Plasma lipid transfer proteins. *Annu. Rev. Biochem.* 64, 235–257 (1995).
35. Brown, M. L. et al. Molecular basis of lipid transfer protein deficiency in a family with increased high-density lipoprotein. *Nature* 342, 448–451 (1989).
36. Bruce, C., Beamer, L. J. & Tall, A. R. The implications of the structure of the bactericidal/permeability-increasing protein on the lipid-transfer function of the cholesteryl ester transfer protein. *Curr. Opin. Struct. Biol.* 8, 426–434 (1998).
37. Huuskonen. J. et al. Structure and phospholipid transfer activity of human PLTP: analysis by molecular modeling and site-directed mutagenesis. *J. Lipid Res.* 40, 1123–1130 (1999).
38. Okamoto, H. et al. A cholesteryl ester transfer protein inhibitor attenuates atherosclerosis in rabbits. *Nature* 496, 203–206 (2000).
39. Rinninger, F. et al. Probucol enhances selective uptake of HDL-associated cholesteryl esters in vitro by a scavenger receptor B-I-dependent mechanism. *Arterioscler. Thromb. Vasc. Biol.* 19, 1325–1332 (1999).
40. Matthews, C. M. E. The theory of tracer experiments with $^{131}$I-labeled plasma proteins. *Phys. Med. Biol.* 2, 36–53 (1957).
41. Honkakoski, P. & Negishi, M. Protein serine/threonine phosphatase inhibitors suppress phenobarbital-induced Cyp2b10 gene transcription in mouse primary hepatocytes. *Biochem. J.* 330, 889–895 (1998).
42. He, T. et al. A simplified system for generating recombinant adenoviruses. *Proc. Natl. Acad. Sci. USA.* 95, 2509–2514 (1998).
43. Lu, L. et al. Adenoviral delivery of CTLA4Ig into myeloid dendritic cells promotes their in vitro tolerogenicity and survival in allogeneic recipients. *Gene Ther.* 6, 554–563 (1999).
44. Tall, A. R. Plasma cholesterol ester transfer protein. *J. Lipid Res.* 34, 1255–1274 (1993).
45. Lagrost, L. Regulation of plasma cholesterol ester transfer protein (CETP) activity: review of in vitro and in vivo studies. *Biochem. Biophys. Acta.* 1215, 209–236 (1994).

What is claimed is:

1. A method of decreasing apolipoprotein B-containing lipoprotein or triglyceride in a subject which comprises administering to the subject an amount of a compound effective to decrease plasma phospholipid transfer protein activity and thereby decrease apolipoprotein B-containing lipoprotein or triglyceride.

2. The method of claim 1, wherein the decrease in apolipoprotein B-containing lipoprotein requires low density lipoprotein receptor activity.

3. A method of treating dyslipidemia or cardiovascular disease in a subject which comprises administering to the subject an amount of a compound effective to decrease plasma phospholipid transfer protein activity and thereby treat the subject's dyslipidemia or cardiovascular disease.

4. The method of claim 3, wherein the dyslipidemia occurs in familial hyperlipidemia, obesity, or diabetes.

5. The method of claim 3, wherein the cardiovascular disease is atherosclerosis.

6. The method of claim 1, wherein the compound decreases cholesteryl ester transfer protein activity.

7. The method of claim 6, wherein the compound increases high density lipoprotein.

8. A method of identifying a chemical compound which decreases apolipoprotein B-containing lipoprotein or triglyceride, which comprises contacting cells expressing plasma phospholipid transfer protein (PLTP), or contacting an extract from said cells, with the chemical compound under conditions suitable for decreasing PLTP activity, and detecting a decrease in PLTP activity in the presence of the chemical compound so as to thereby identify the chemical compound as a compound which decreases apolipoprotein B-containing lipoprotein or triglyceride, wherein a decrease in PLTP activity results in decreased apolipoprotein B-containing lipoprotein or triglyceride.

9. The method of claim 8, wherein the compound decreases cholesteryl ester transfer protein activity.

10. The method of claim 9, wherein the compound increases high density lipoprotein.

11. The method of claim 8, wherein the cells are liver cells or liver cancer cells.

12. The method of claim 8, wherein the cells are vertebrate cells.

13. The method of claim 12, wherein the vertebrate cells are mammalian cells.

14. The method of claim 13, wherein the mammalian cells are human cells.

15. A compound identified by the method of claim 8.

16. A pharmaceutical composition comprising (a) an amount of a chemical compound identified using the method of claim 8, or a novel structural and functional homolog or analog thereof, effective to reduce PLTP activity and (b) a pharmaceutically acceptable carrier.

17. A method for preparing a composition which comprises admixing a carrier and a pharmaceutically effective amount of a chemical compound identified by the method of claim 8, or a novel structural and functional analog or homolog thereof.

18. A method for making a composition of matter which decreases apolipoprotein B-containing lipoprotein or triglyceride, which comprises identifying a chemical compound using the method of claim 8, and then synthesizing the chemical compound or a novel structural and functional analog or homolog thereof.

19. A method of treating a subject with elevated apolipoprotein B-containing lipoprotein or elevated triglyceride, which comprises administering to the subject a therapeutically effective amount of a chemical compound identified by the method of claim 8, or a novel structural and functional analog or homolog thereof.

20. A method of preparing a composition which comprises identifying a chemical compound which decreases apolipoprotein B-containing lipoprotein or triglyceride using the method of claim 8, and admixing the identified chemical compound with a carrier.

* * * * *